Figure 1:
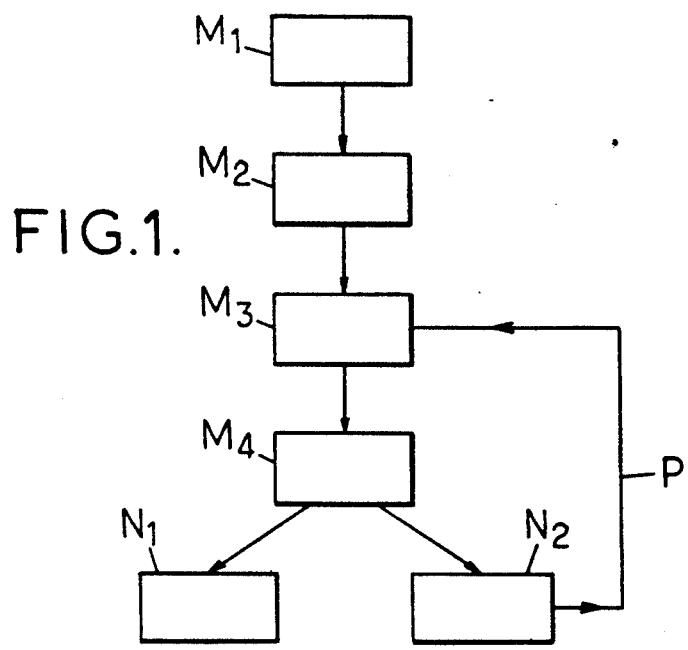

United States Patent [19]

Leleu et al.

[11] Patent Number: 5,238,826
[45] Date of Patent: Aug. 24, 1993

[54] PROCESS FOR MANUFACTURING XYLOSE

[75] Inventors: Jean-Bernard Leleu; Pierrick Duflot, both of Lestrem; Jean-Jacques Caboche, Bethune, all of France

[73] Assignee: Roquette Freres, France

[21] Appl. No.: 537,459

[22] Filed: Jun. 14, 1990

[30] Foreign Application Priority Data

Jun. 16, 1989 [FR] France .................. 89 08046

[51] Int. Cl.$^5$ .............................. C12P 19/02
[52] U.S. Cl. .................... 435/105; 435/233; 435/234; 435/274; 435/276; 435/803; 435/938; 435/255.5; 536/124; 536/125; 536/127
[58] Field of Search ............. 435/105, 233, 234, 254, 435/255, 274, 276, 803, 938; 536/124, 125, 127

[56] References Cited

U.S. PATENT DOCUMENTS

| | | | |
|---|---|---|---|
| 3,607,652 | 9/1971 | Ueda | 435/938 |
| 3,619,369 | 11/1971 | Onishi et al. | 435/938 |
| 4,394,178 | 7/1983 | Chao et al. | 127/55 |
| 4,490,468 | 12/1984 | Gong et al. | 435/162 |

FOREIGN PATENT DOCUMENTS 1518510 9/1968 France .

OTHER PUBLICATIONS

Journal of Chromatography, vol. 437, 1988, pp. 387-397; J. O. Baker et al.: "Degradation of ketoses during aqueous high-performance liquid chromatography on lead-form cation-exchange resins".
Journal of Fermentation Technology, vol. 63, No. 4, 1985, pp. 331-335; S. Ohmomo et al.: "Biotransformation of D-xylulose to D-xylose by immobilized enzyme prepared from *Streptomyces flavorirensis*".
Izumori et al., *J. Ferment. Tech.*, vol. 66(1), pp. 33-36, 1988.

Primary Examiner—Ronald W. Griffin
Assistant Examiner—Pamela S. Webber
Attorney, Agent, or Firm—Larson and Taylor

[57] ABSTRACT

Process for manufacture of D-xylose characterized by the fact that:

in a first step, syrup of D-xylulose is subjected to an enzymatic isomerization in $M_3$ providing a mixture of D-xylose and D-xylulose, in a second step, the abovesaid mixture is subjected to chromatographic treatment in $M_4$ leading to at least two fractions of which one is highly enriched in D-xylose (fraction $X_1$) et of which the other is highly enriched in D-xylulose (fraction $X_2$), in a third step; the fraction $X_2$ is recycled through a pipe P to $M_3$, the D-xylose being recovered from the fraction $X_1$, the latter can also be subjected directly to a hydrogenation step.

11 Claims, 2 Drawing Sheets

PROCESS FOR MANUFACTURING XYLOSE

The invention relates to a process for manufacturing D-xylose.

It is known to prepare D-xylose from raw materials such as birch wood, corn cobs, shells of seeds or almonds.

By acid hydrolysis of these raw materials, under extreme conditions of temperature and of pressure, the xylans—polymers of D-xylose—are decomposed into xylose of which the essential application is the manufacture—by hydrogenation—of xylitol.

This process suffers however from many drawbacks the principal of which are:

the low content of xylans of raw materials, which is manifested by low yields of xylose (from 8 to 15% by weight of the raw material employed) and by the generation of a considerable amount of by-products for which it is difficult, even illusory to find a value enhancement and whose disgarding is found to be very polluting, the presence in the hydrolysates of these raw materials of other sugars than xylose, namely those of the group comprising glucose, mannose, galactose and arabinose whose physical properties are close to those of D-xylose (the physical properties of the hydrogenated equivalents of these sugars are close to those of xylitol), which renders very difficult the separation of this D-xylose (and, as the case may require, of the xylitol); now, the presence of galactitol, which is found normally in the hydrolysates of hydrogenated woods and which crystallizes at the same time as the xylitol when the syrups are concentrated, is undesirable when the xylitol is intended for foodstuffs since said galactitol causes cataract.

French patent No. 2,009,331, which describes a process for manufacturing D-arabitol by fermentation particularly of glucose, indicates that D-arabitol is an important raw material for preparing D-xylose by passing through D-xylulose; this patent however remains silent on the means which can be employed to convert the D-xylulose into D-xylose, only pentose (with its optical isomer L-xylose) providing 100% of xylitol by hydrogenation.

It is true that the partial isomerization by chemical route of D-xylulose into D-xylose may be considered but it has the drawback of introducing dangerous solvents Enzymatic isomerization therefore seems preferable. Besides, HOCHSTER and WATSON (National Research Council No. 3105 Ottawa, Canada) have performed by means of enzymes capable of effecting the conversion of D-xylose into D-xylulose and vice-versa, experimentally, the isomerization of D-xylulose into D-xylose, but this without isolating the D-xylose in a state of high purity and under conditions of temperature and especially of concentration which are totally incompatible with employment on the industrial scale.

In addition, the conversion effected by means of these enzymes, like chemical isomerization, is only partial; these isomerizations only enable D-xylose to be obtained with a maximum yield of 75% and 25% of the D-xylulose are thus irremediately lost since it is not converted into D-xylose.

To separate D-xylose from D-xylulose, it has been proposed (French patent No. 2,117,558) to chromatograph a syrup containing these two sugars on an anionic resin charged in the bisulfite form. Separation of the sugars is good under these conditions; but the drawback of this technique resides in the fact that a portion of the D-xylose is bound irreversibly to the resin and that it is difficult to perform more than five consecutive separation cycles without experiencing a notable drop in performances (S. P. Olivier and P. J. du Toit, Biotechnology and Bioengineering, vol. XXVIII, pages 684–699 (1986)].

It has also been proposed, since 1972, by Japanese patent application No. 47-13707, to prepare xylitol without passing through xylose by hydrogenating directly the D-xylulose obtained by double aerobic fermentation from glucose. The drawback of this process resides in the fact that said hydrogenation only provides 50% of xylitol at the same time as 50% of D-arabitol, the latter being, when it is present in such proportions, difficult to separate from the xylitol.

Consequently, there still exists no process enabling the production on an industrial scale of D-xylose or of xylitol with sufficient purity and yield from xylulose, which itself can only be obtained with a low yield, in vicinity of 40%, from D-glucose by passing through D-arabitol.

It is therefore particularly an object of the invention to provide a process for the preparation of D-xylose from D-xylulose, itself obtained from D-glucose, suitable for ending up with D-xylose with a sufficiently high yield and purity for the industrial manufacturer to be able to put up with many steps leading from D-glucose to the desired final product.

And it is to this problem posed for nearly twenty years that Applicants have had the merit of contributing a solution by finding that it was possible to isolate in the state of high purity D-xylose from a mixture of D-xylose and D-xylulose by resorting to chromatography on cationic resins or zeolites, the cationic resins being preferred and constituted especially by those which are used for the chromatographic separation of glucose and of fructose.

Accordingly the process of manufacturing D-xylose according to the invention is therefore characterized by the fact that:

in a first step, a syrup of D-xylulose is subjected to an enzymatic isomerization providing a mixture of D-xylose and D-xylulose, in a second step, said mixture is subjected to chromatographic treatment leading to at least two fractions of which one is highly enriched in D-xylose (fraction $X_1$) and of which the other is highly enriched in D-xylulose (fraction $X_2$), in a third step, the fraction $X_2$ is recycled to the isomerization step, the D-xylose being recovered from the $X_1$ fraction, the latter being also subjected directly to a hydrogenation step.

The D-xylulose may be obtained in a manner known in itself and particularly by microbiological oxidation of D-arabitol which constitutes thereof besides the preferred production process, said D-arabitol being obtained by aerobic fermentation of D-glucose.

According to an advantageous embodiment, the process for manufacturing D-xylose according to the invention is therefore characterized by the fact that the starting D-xylulose is prepared by a succession of steps comprising:

an aerobic fermentation of a syrup of D-glucose by means of an osmophilic microorganism of the Pichia genus, converting the D-glucose into D-arabitol, an aerobic fermentation of the D-arabitol syrup by means of a microorganism producing alcohol dehydrogenase, of the Acetobacter, Gluconobacter or Klebsiella genus, suitable for converting D-arabitol into D-xylulose, an isomerization of the D-xylulose syrup under the action of the glucose isomerase or of the xylose isomerase, into a D-xylose rich syrup.

The aerobic fermentation of the glucose may be replaced by a modification consisting of passing by the oxidation of the glucose into gluconic acid which, in its calcium salt form, can be decarboxylated by the so-called RUFF method to give D-arabinose (cf. U.S. Pat. No. 3,755,294). The D-arabinose is then hydrogenated in a manner known in itself to provide D-arabitol.

In spite of its apparent complexity, the process according to the invention enables, by means of the particular combination of its constituent steps, the production of the D-xylose with a yield greater than 30% with respect to the starting D-glucose which is a raw material which is abondant and of low price.

With respect to the processes of the prior art,
the amounts of raw material to employ and
the pollution as well as the volume of by-products generated by the manufacture of the D-xylose and consequently of xylitol
are considerably diminished.

Other advantages reside in the fact:
that the logistic problems relating to the collection of the raw material, the D-glucose, do not exist,
that the processing of this raw material can be carried out in conventional equipment which do not have to withstand extremely high temperatures and pressures neither corrosive media,
that the D-xylose is obtained free from galactose; the xylitol obtained by hydrogenation does not therefore contain galactitol and can, consequently, be used in foodstuffs.

The invention will be better understood by means of the additional description which follows, of non-limiting examples and of the accompanying drawing, said additional description, examples and drawing relating to advantageous embodiments.

Figure 3:
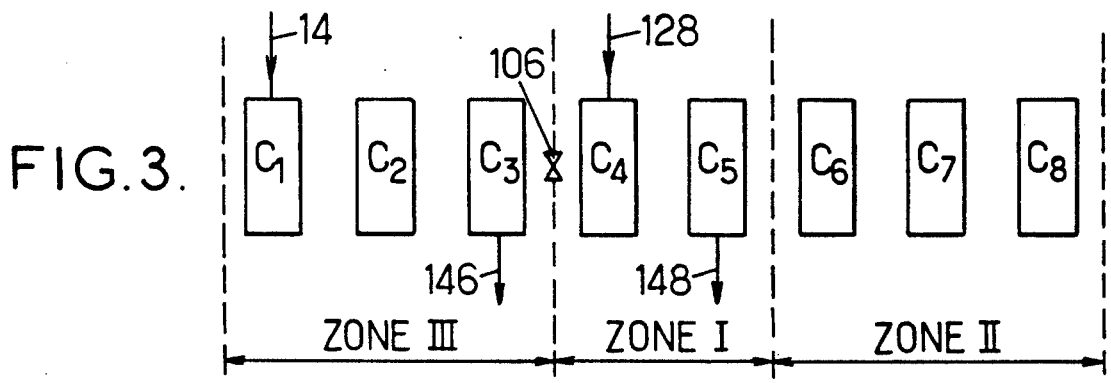
Figure 4:
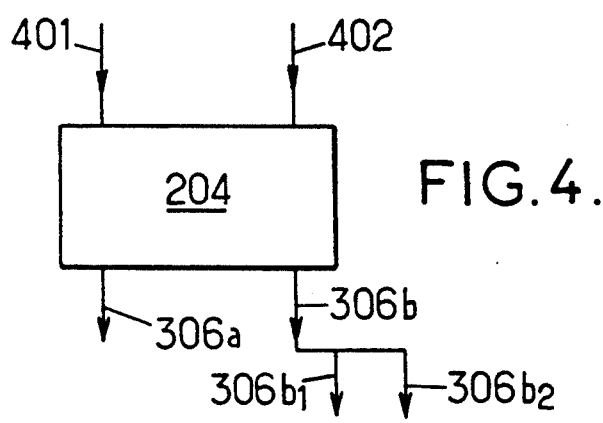
Figure 2:
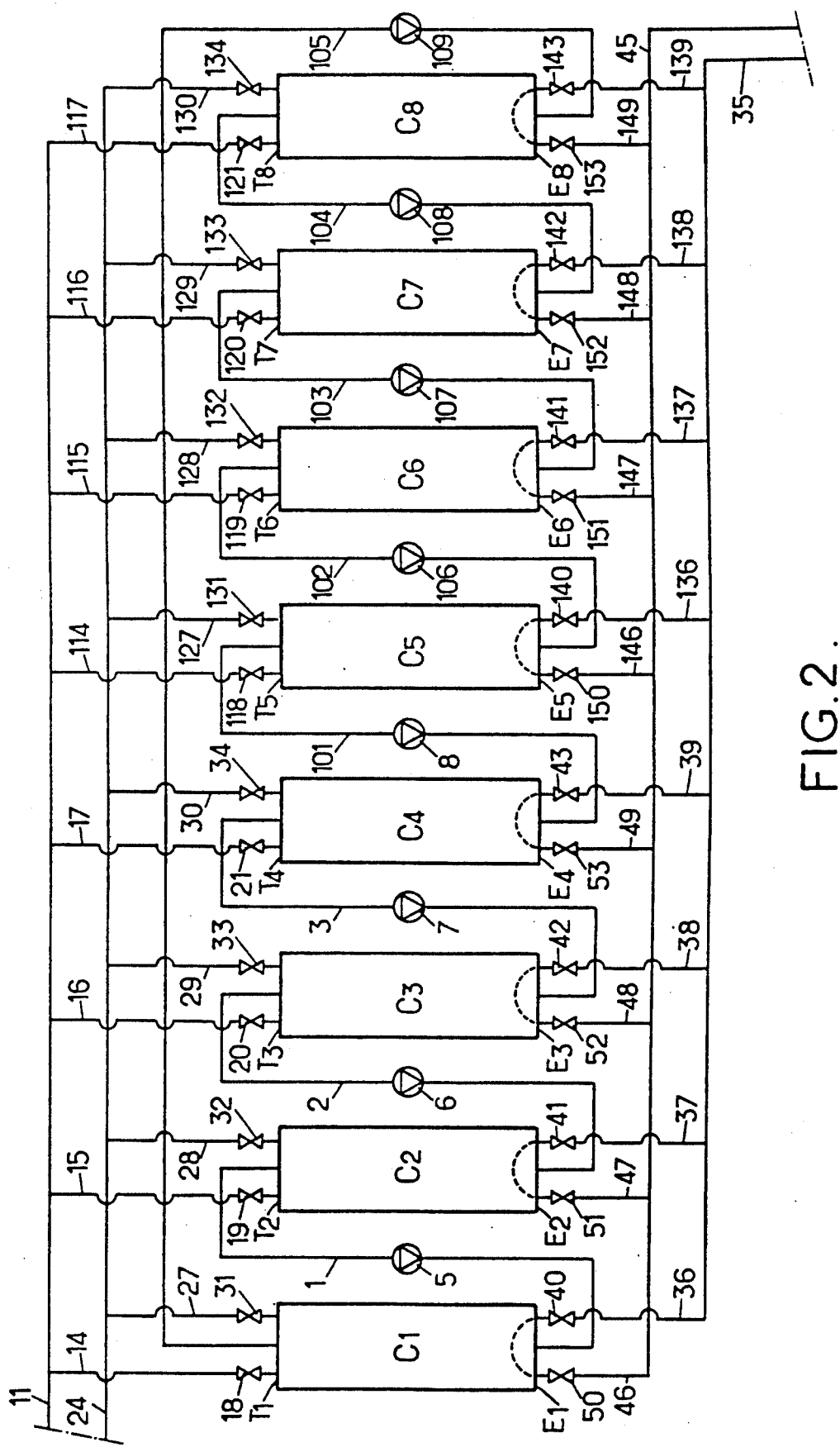

In the above-said drawing,

FIG. 1 shows diagrammatically the course of the process according to the invention, FIGS. 2 to 4 show diagrammatically the parts of an installation suitable for the practicing of said process.

In FIG. 1 of the accompanying drawing, the course of the abovesaid process is shown diagrammatically, namely:

the conversion of D-glucose into D-arabitol at $M_1$, the conversion of D-arabitol into D-xylulose at $M_2$, the chromatographic treatment of the isomerized syrup at $M_4$, the recovery of a syrup rich in D-xylose at $N_1$ and that of a syrup rich in D-xylulose at $N_2$, the recycling from $N_2$ to $M_3$ through a pipe P of the syrup rich in D-xylulose.

For the fermentation of the glucose, it is possible to resort to a culture medium having the following composition:

| | |
|---|---|
| dextrose | 150 to 200 g/l |

-continued

| | |
|---|---|
| organic nitrogen (in the form of corn-steep or yeast extract) | 2 to 4 g/l (N × 6.25) |
| $KH_2PO_4$ | 1 to 3 g/l |
| $MgSO_4, 7H_2O$ | 1 to 2 g/l | and which is introduced into a fermenter, sterilized then inoculated by means of about 10% of a 24 hours culture of a microorganism of Pichia genus, for example of the strain Pichia Ohmeri No. 20,209 preserved at the A.T.C.C. ( or of the strain of Pichia farinosa), this culture having been produced on a medium constituted, for example, as follows:

| | |
|---|---|
| glucose | 50 g/l |
| yeast extract | 10 g/l |
| $KH_2PO_4$ | 3 g/l |
| $MgSO_4, 7H_2O$ | 1 g/l |

The fermentation is continued at a temperature close to 30° C. for 80 to 100 hours under aeration corresponding to 1 to 1.5 volume of air/volume of culture/minute, and at a pH comprised between 4 and 6, preferably close to 4.5, advantageously maintained by ammonia, due to which there is generally obtained a content of arabitol of 65 to 90 g/l, this arabitol representing from 70 to 85% of sweet matter present in the culture medium at the end of this fermentation.

The yield of arabitol with respect to the glucose employed is about 40 to 50%.

The entire contents of the fermenter (fermentation broth rich in arabitol) is then sterilized so as to destroy the yeast; it is then seeded for the step of fermentation of the D-arabitol by an inoculum (10% approximately) of a culture of Acetobacter suboxidans cultivated for about 20 hours on a medium having the following constitution:

| | |
|---|---|
| arabitol | 50 g/l |
| sorbitol | 2 g/l |
| yeast extract | 2 g/l |
| $KH_2PO_4$ | 0.2 g/l |
| $MgSO_4, 7H_2O$ | 0.2 g/l |
| $CaCO_3$ | 5 g/l |

It is advantageous to subject the fermentation broth rich in arabitol to a purification by centrifugation of filtration before seeding by the Acetobacter.

The fermentation of the D-arabitol is continued without any other nutrient substances at a temperature of 20° to 40° C., under aeration corresponding to 1 to 1.5 volume of air/volume of culture/minute, at a pH of 4.0 to 6.0 and for a time generally comprised between 24 and 48 hours, after which a must rich in D-xylulose is obtained, this D-xylulose representing from 70 to 85% of the sweet matter present at the end of the second fermentation.

The sweet impurities present at this stage are principally constituted from D-arabitol which has escaped oxidation by the Acetobacter and the xylitol formed in parallel with the arabitol in the course of the first fermentation; there is also found among these impurities sugars like lyxose and some traces of glucose or of various saccharides which were present in the state of impurities in the dextrose which served as raw material.

The glucid composition of the fermentation broth obtained at the end of the step of fermentation of the D-arabitol is as follows:

| xylulose | 70 to 85% |
|---|---|
| arabitol | 5 to 15% |
| xylitol | 1 to 5% |
| various saccharides | 5 to 10%. |

This fermentation must may be purified in manner known in itself (by filtration, decoloration on active charbon and demineralization) then concentrated before being subjected to the isomerization step.

It may be obligatory to resort to the abovesaid purification if the isomerization is performed continuously by means of an enzyme immobilized in a piston effect reactor; this purification is superfluous in the case where batch isomerization follows with lost enzyme and discontinuously.

For the isomerization step a commercial xylose isomerase may be used of the type of those employed for the manufacture of corn syrups with high fructose content, namely, for example:

that which is known under the brand SPEZYME and which is marketed by Suomen Sokeri, that which is known under the brand LYSASE GI 2000 and which is manufactured by Applicant's Company (French patent No. 2,353,562).

Preferably, the amount of enzyme employed is such that the equilibrium of the reaction is reached in 4 to 48 hours; the presence of a protective agent for the enzyme such as sodium bisulfite and/or a magnesium salt is desirable.

The isomerization is conducted at a temperature of 40° to 80° C. and at a pH comprised between 6.0 and 8.5.

Generally, the parameters of the isomerization step are selected such that the latter results in a syrup having a D-xylose content greater than 53%.

At the end of the isomerization step, the glucide composition of the isomerized syrup obtained is generally as follows:

| xylose | 53 to 64% |
|---|---|
| xylulose | 17 to 22% |
| arabitol | 5 to 15% |
| xylitol | 1 to 5% |
| various saccharides | 5 to 10%. |

It has been observed with surprise that the presence of xylitol formed in parallel with the arabitol during the fermentation of the glucose and unconverted at the time of fermentation of the D-arabitol does not disturb the operation of the isomerase xylose since the maximum proportions of xylose are identical (close to 75%) with the proportions obtained previously in the isomerization of pure xylose.

This fact is all the more unexpected as in 1988, IZUMORI and TUZAKI, "J. Ferment. Technol.", vol. 66, no. 1, 33-36 (1988), wrote that it seemed indeed that xylitol is a competitive inhibitor of isomerase xylose ; its presence alone in syrups objected to isomerization would have seriously interfered with the isomerization reaction, making it thereby impossible to perform the process according to the invention.

The xylose rich syrup obtained after isomerization may be purified by demineralization and is then subjected to the chromatographic fractionation step.

This chromatographic fractionation step may be performed in a manner known in itself, discontinuously or continuously (a simulated moving bed), on adsorbents of the strongly acid cationic resin type, preferably charged with alcaline or alcaline-earth ions or again of the cationic zeolite type charged with $NH_4^+$, $Na^+$, $K^+$ and $Ca^{2+}$, $Ba^{2+}$ ions and the like.

Examples of such chromatographic separation processes are given in U.S. Pat. Nos. 3,044,904; 3,416,961; 3,692,582; FR 2,391,754; FR 2,099,336; U.S. Pat. Nos. 2,985,589; 4,024,331; 4,226,977; 4,293,346; 4,157,267; 4,182,623; 4,332,623; 4,405,445; 4,412,866 and 4,422,881.

According to a preferred embodiment, the chromatographic separation step is performed by employing the process and the apparatus described in the U.S. Pat. No. 4,422,881 and its corresponding French patent 2,454,830 of which Applicant is owner.

Whatever the chromatographic separation process used, recourse is had, as adsorbent, to a cationic material, preferably to a strongly cationic resin, this resin being more preferably still employed in the calcium ion form and having a content in divinylbenzene of about 4 to 10%.

The choice of the parameters of the chromatography step, among which are particularly:

the elution flow rate, the supply flow rate of isomerized syrup, the extraction flow rate of the fraction enriched in xylose, the composition of the zones of desorption, adsorption and enrichment, is explained and illustrated in the example.

This choice is made so that the fraction $X_1$ shows a richness in D-xylose, the percentages being expressed by weight to dry matter:

from 60 to 95%, preferably, from 75 to 90% and, more preferably still, from 80 e,gra/a/ 85%, and a content of D-xylulose below 25% and, preferably, below 15%.

To arrive at this result, said parameters are selected as follows when the chromatography step is performed by using the process and the apparatus described in the U.S. Pat. No. 4,422,811 and when the adsorbent used is a low granulometry cationic resin, cross-linked with 6% of divinylbenzene and used in the calcium form:

elution flow rate of 125 to 500 l/h/m³ of adsorbent, flow rate of isomerized syrup supply of 15 to 60 l/h/m³ of adsorbent, flow rate of extraction of the fraction enriched in xylose from 30 to 120 l/h/m³ of adsorbent.

The chromatography step leads moreover to the concomitant production of a fraction $X_2$ highly enriched in xylulose and that of a fraction $X_3$ composed of products very highly adsorbed by the cationic material or, on the contrary, strongly excluded.

Among the products strongly adsorbed by the cationic material, are found especially the xylitol and the arabitol and, among the products strongly excluded, the various saccharides.

The fraction $X_2$ highly enriched in D-xylulose has preferably the following composition, the percentages being expressed by weight to dry matter:

from 50 to 80% of xylulose, from 20 to 50% of xylose, from 0 to 5% of arabitol and xylitol.

This fraction $X_2$ highly enriched in D-xylulose is recycled, according to the invention, to the enzymatic isomerization step.

It is due to the employment according to the invention of the chromatographic separation and recycling steps that it has become possible to convert with an extremely high yield the D-xylulose into D-xylose whilst obtaining this D-xylose in a state of a high purity, which renders the manufacture of the D-xylose from the D-glucose through D-xylulose, economically interesting.

The fraction $X_3$ bringing together the products very highly adsorbed by the resin or, on the contrary, very strongly excluded, is removed from the system.

From the fraction $X_1$ very rich in D-xylose, the D-xylose is recovered. It is also possible to subject the fraction $X_1$ directly to a hydrogenation particularly catalytic.

To recover the D-xylose from the fraction $X_1$, it is possible:

either to concentrate syrup to separate the chemically pure D-xylose by crystallization, the exhausted mother-liquors can then advantageously be recycled to the chromatographic step, or to dehydrate in its totality said syrup to provide D-xylose of technical quality.

When it is decided to hydrogenate the fraction $X_1$ directly, recourse is had to the conditions known in the prior art, particularly to catalysts with ruthenium or with Raney nickel; this direct hydrogenation is employed preferably when it is desired to manufacture xylitol; the hydrogenation can be carried out with a Raney nickel catalyst, under a hydrogen pressure comprised between 20 and 80 kg/cm² and a temperature of about 80° to 130° C.

The xylitol syrup obtained has the following composition:

| xylitol | 87 to 97% |
|---|---|
| arabitol | 3 to 13%. |

Its very great richness in xylitol enables separation of the xylitol by crystallization directly from its aqueous solution with a very high yield and in a very high state of purity and it is possible to exhaust in practice the mother-liquors from the crystallization by carrying out several consecutive crops, as is indicated, for example, in French patent No. 2,202,069.

EXAMPLE

Step of aerobic fermentation of D-glucose

In a fermenter of total capacity 10 m³, are introduced:

| 1200 kg of crystallized dextrose monohydrate, |
| 16 kg of yeast extract, |
| 8 kg of KH$_2$PO$_4$, |
| 8 kg of MgSO$_4$, 7H$_2$O. |

After sterilization of the culture medium and cooling to 30° C., this fermenter is inoculated by means of 800 liters of a preculture of Pichia Ohmeri ATCC 20,209 such as described in French patent No. 2,009,331, which preculture is aged 24 hours.

The aeration was continued throughout the duration of the transformation of the glucose into arabitol either for 90 hours with a flow rate of 130 Nm³/hour and the pH was checked by the addition of ammonia to a value of 4.5.

Step of aerobic fermentation of D-arabitol

This first step having been completed, the content of the fermenter was sterilized; then, without the addition of other nutrient ingredients and after cooling to a temperature of 30° C., it was again seeded, but this time by means of 800 liters of a preculture aged 24 hours of suboxydans Acetobacter cultivated on a medium of the following composition:

| arabitol | 50 g/l |
|---|---|
| sorbitol | 2 g/l |
| yeast extract | 2 g/l |
| KH$_2$PO$_4$ | 0.2 g/l |
| MgSO$_4$, 7 H$_2$O | 0.2 g/l. |

At the end of fermentation, the culture must was filtered, decolorized on active coal and demineralized on ion exchange resins.

The glucid composition of this purified syrup was revealed to be the following:

| xylulose | 80.7% |
|---|---|
| arabitol | 6.5% |
| xylitol | 3.8% |
| various saccharides | 9%. |

The syrup was obtained with a yield of 48% with respect to the dry matter of glucose employed, which corresponds to a yield of 40% of pure xylulose with respect to the glucose employed.

Isomerization step

The purified syrup obtained after the aerobic fermentation step of the D-arabitol was concentrated at 45% of dry matter, then it was introduced into a thermostatic tank at 55° C. in the presence of glucose isomerase of the trademark SPEZYME marketed by Suomen Sokeri. The dose of enzyme employed was 2 kg for the 2 m³ of syrup present in the tank. The pH of the syrup was adjusted to 7.0 and the isomerization reaction took place for 24 hours in the presence also of 0.7 ml of NaHSO$_3$ in 30% solution and of 1 g/l of MgSO$_4$, 7H$_2$O.

At the end of this step, the syrup obtained had the following composition:

| xylose | 60% |
|---|---|
| xylulose | 20% |
| arabitol | 6.5% |
| xylitol | 3.8% |
| various saccharides | 9.7%. |

The proportion of xylulose with respect to the xylose in the syrup was hence 25%, which was the normal equilibrium value of the enzyme when isomerization is performed starting from pure crystalline xylose. It was therefore observed, as has already been stated, that the xylitol has not behaved like a competitive inhibitor of the isomerization enzyme.

Chromatographic fractionation step

Fractionation of the isomerized syrup rich in xylose followed in the continuous chromatographic separation installation of which the details of construction and of operation are described in U.S. Pat. No. 4,422,881 and in the corresponding French patent No. 2,454,830, these details only being taken up again here to the extent required for understanding of the description.

This installation comprises, as shown in FIG. 2 of the U.S. patent (taken up again here in FIG. 2, for the detailed explanation of which reference will be made to the U.S. patent), eight columns or stages $C_1$ to $C_8$ of 200 liters each, filled with adsorbent of the strong cationic resin type in the calcium form and of fine granulometry (0.2 to 0.4 millimeter) of Duolite C204-2078 type.

The column $C_5$ is connected to the column $C_4$ through a pipe 101, the columns $C_5$ to $C_8$ are connected together by pipes 102, 103, 104 and the column $C_8$ is connected to the column $C_1$ through a pipe 105.

The pipes 102 to 105 are individually equipped with check valves 106, 107, 108 and 109.

The sides or extremities of columns $C_5$ to $C_8$ corresponding to the feeding are marked by $T_5$, $T_6$, $T_7$ and $T_8$, those corresponding to the extraction by $E_5$, $E_6$, $E_7$ and $E_8$.

The columns $C_5$ to $C_8$ are connected in parallel to the pipe 11 through pipes 114, 115, 116 and 117 respectively equipped with electrovalves 118, 119, 120 and 121.

They are connected in parallel to the pipe 24 by pipes 127, 128, 129 and 130 respectively equipped with electrovalves 131, 132, 133 and 134.

They are connected to the collecting pipe 35 in parallel by pipes 136, 137, 138 and 139 respectively equipped with electrovalves 140, 141, 142 and 143 and to the collecting pipe 45 in parallel by pies 146, 147, 148 and 149 equipped respectively with electrovalves 150, 151, 152 and 153.

From a general point of view, it is underlined that the ratio height/diameter of the columns equipping the installation is selected between 3 and 0.3, preferably between 2 and 0.5.

By adjustment of the electrovalves, there were established in this installation a desorption zone I of two stages, an adsorption zone II of 3 stages and a zone III of enrichment and separation of the weakly adsorbed xylose and of the strongly adsorbed xylitol and arabitol of 3 stages, as shown by FIG. 3 which is a diagrammatic drawing of the installation according to FIG. 2 and in which there is only shown:

the columns $C_1$ to $C_8$, the closure device, in the event the electrovalve 106, the supply pipes for xylose rich isomerized syrup to be fractionated and for water, shown respectively at 14 and 128, and the extraction pipe 148 for syrup enriched in xylulose (fraction $X_2$), on the one hand, and the pipe 146 for successively extracting xylitol-arabitol (fraction $X_3$), various saccharides (fraction $X_3$) and xylose (fraction $X_1$), on the other hand.

The closure device 106 (especially an electrovalve) maintains in the configuration adopted, a total full tightness between, on the one hand, the zone III, which is an enrichment zone at the end of which are therefore recovered successively the remainder of the strongly adsorbed xylitol-arabitol, various saccharides, then the fraction enriched in xylose and, on the other hand, zone I of xylulose desorption, at the head of which zone is introduced the desorption water.

This closure device ensures the direction of passage of the liquid phase over the selective adsorbent.

A timing device adjusted to 26'30" ensures for the flow rates indicated below a supply of water to the first stage or first column of the desorption zone I sufficient to effect the desorption of the totality of xylulose, and a supply of a volume of isomerized syrup rich in xylose compatible with the adsorbent volume and its adsorption capacity, so as to obtain an extraction ratio of xylose at least equal to 60% of xylose present in the isomerized syrup and this to a richness at least equal to 60% of xylose.

The above-mentioned extraction ratio and purities are kept constant by adjusting the flow rate of the extraction pump (not shown) of the adsorbed xylulose. The outflow of the "arabitol-xylitol-various saccharides" fractions (fraction $X_3$) then "enriched xylose" (fraction $X_1$) is effected at atmospheric pressure and its constant flow rate results from the difference between the supply flow rates and the extraction flow rate.

The xylose rich isomerized syrup which is introduced into the installation at the head of the zone of enrichment and separation III, shows, as indicated above, a content of dry matter of 50%. The temperature within the separation columns is kept at about 70° C.

FIG. 4 shows diagrammatically at 204 the installation of FIGS. 2 and 3, the same reference numerals denoting the same elements for the common parts as in FIG. 1. The chromatography installation 204 comprises a pipe 306$b$ through which are removed the excess of water containing a large fraction of arabitol-xylitol and the various saccharides fraction (fraction $X_3$). These extracts are with low content of dry matter and immerge through the pipe 306$b_1$.

The supply of water is effected through a pipe 401.

The arrows born on the pipes indicate the direction of flow.

The chromatography unit 204 operates as follows:

the xylose rich isomerized syrup which has to be subjected to chromatographic fractionation is led through the pipe 401 at a flow rate of 52 liters/hour and has a content of dry matter of 50%, the enriched xylose (fraction $X_1$) is recovered through the pipe 306$b_2$ with a flow rate of 88.5 liters/hour, its average content of dry matter being 23.3%, the total amount of liquids extracted besides from the installation is with a total flow rate of 344.5 liters/hour, composed of:

on the one hand,

* an excess Water fraction, extracted through the pipe 306$b_1$, containing at low concentration and high purity, xylitol-arabitol then, at low concentration and at high richness, the various saccharides (fraction $X_3$), the whole representing an equivalent of 265.5 liters/hour, the content of dry matter being 2.5%; these fractions correspond to the 20 first minutes of the cycle,

* of a fraction of highly enriched xylose (fraction $X_1$), of an equivalent of 88.5 liters/hour, led through a pipe 306$b_2$ to a purification installation (not shown), the content of dry matter of this fraction being 23.3%; this fraction corresponds to the last part of the cycle namely 6'30", and, on the other hand, a fraction highly enriched in xylulose and much impoverished in xylose (fraction $X_2$), extracted at a flow rate of 79 liters/hour through the pipe 306$a$ (FIG. 4) corresponding to the pipe 148 of FIG. 3.

Tables 1 et 2 below summarize the conditions characterizing the operation of the chromatographic fractionating device.

TABLE 1

| Chromatographic inputs | Xylose rich syrup | Water | Total |
|---|---|---|---|
| Flow rate | 52 l/h | 381 l/h | 433 l/h |
| Density | 1.25 | | |
| Dry matter | 50% | | |
| Flow rate by weight | 32 kg/h | | |
| Richness in xylose | 60% | | |
| Flow rate by weight of xylose | 19.2 kg/h | | |
| Flow rate by weight of xylulose | 6.4 kg/h | | |

TABLE 2

| Chromatographic outflows | Xylose enriched fraction($X_1$) | Xylulose enriched fraction($X_2$) | Arabitol + xylitol + various saccharides ($X_3$) | Total |
|---|---|---|---|---|
| Flow rate | 88.5 l/h | 79 l/h | 265.5 l/h | 433 l/h |
| Density | 1.08 | 1.02 | 1.01 | |
| Dry Matter | 23.3% | 5.9% | 2.5% | |
| Flow rate by weight | 20.7 kg/h | 4.7 kg/h | 6.6 kg/h | 32 kg/h |
| Richness in xylose | 84% | 32% | 5% | |
| Flow rate by weight of xylose | 17.4% kg/h | 1.5 kg/h | 0.3 kg/h | 19.2 kg/h |
| Content of xylulose | 15% | 68% | 0% | |
| Flow rate by weight of xylulose | 3.2 kg/h | 3.2 kg/h | 0 | |

This result corresponds to an extraction ratio by weight of xylose of 20.7/32=65% of enriched syrup with 84% of xylose, which represents an extraction ratio of the xylose of 17.4/19.2=90.6%, and to an extraction ratio by weight of xylulose equal to 4.7/32=15% of enriched syrup with 68% of xylulose, which represents an extraction ratio of xylulose equal to 3.2/6.4=50%.

It is to be noted that at this level, it would have been possible, for example, to considerably increase this extraction ratio of the xylulose by increasing, for example, the extraction flow rate of the fraction ($X_2$), which would be manifested by a reduction in the flow rate of the outflow of the fractions ($X_1$) and ($X_3$), Correlatively, there would have been obtained a fraction ($X_2$) still richer in xylose but with an extraction yield of the xylose a little less. The fraction ($X_2$) would have on the other hand been a little poorer in xylulose.

Analysis of the enriched xylose syrup fraction ($X_1$) gives the following results:

| xylitol-arabitol | traces |
|---|---|
| xylulose | 15% |
| xylose | 84% |
| various saccharides | 1%. |

Analysis of the enriched xylulose syrup fraction ($X_2$) gives the following results:

| xylitol-arabitol | traces |
|---|---|
| xylulose | 68% |
| xylose | 32%. |

The xylose rich fraction may be subjected to crystallization in manner known in itself after having been purified and concentrated. The crystallized xylose so obtained may be hydrogenated so as to form xylitol.

In this case, after exhaustion of the mother-liquors in xylose, the latter are advantageously recycled to the chromatographic fractionation step so as to extract therefrom practically all the xylose. Thus this fraction was concentrated under vacuum to a dry matter content of 75% in the presence of crystals of D-xylose since it was cooled to a temperature of 20° C. with stirring and in 24 hours. The crystallized mass was drained and washed and the xylose obtained with a 50% yield in a single crop. The purity of this xylose was 98%. The mother-liquors had a richness in xylose of about 68% and could therefore advantageously be recycled to the chromatographic step so as to extract therefrom practically all the xylose.

The fraction rich in xylose may also be hydrogenated directly to provide a syrup rich in xylitol.

Thus this fraction was hydrogenated by means of a Raney nickel catalyst under a hydrogen pressure of 45 bars and at a temperature of 120° C. and provided a syrup with a richness of 91% of xylitol.

The fraction $X_2$ coming from the chromatography step was subjected by recycling once more to the enzymatic isomerization step and this under the same conditions as those already described above with regard to the isomerization of the fermentation broth rich in xylulose An isomerized syrup was then obtained of which the composition was as follows:

| xylitol-arabitol | traces |
|---|---|
| xylulose | 26% |
| xylose | 74%. |

This syrup was mixed again with the syrup rich in xylose and was submitted again to chromatographic fractionation.

It is shown from the numerical values indicated in this example that, due to the process according to the invention, there is obtained, from 131.5 kg of glucidic dry matter coming from the fermentation step of the D-arabitol, an amount of 100 kg of dry matter of xylose syrup with 84% richness, which, taking into account a conversion yield of the glucose to xylulose of 48%, is manifested by a use of glucose of 274 kg.

There is hence obtained with the process of the invention D-xylose in the stage of very rich syrup with a yield of 36% with respect to the glucose employed.

We claim:

1. A process for the manufacture of D-xylose comprising,
   subjecting a syrup of D-glucose to aerobic fermentation by means of an osmophilic microorganism to convert the D-glucose to D-arabitol containing xylitol as an impurity,
   sterilizing the fermentation broth of said D-arabitol and xylitol,
   subjecting said sterilized fermentation broth to aerobic fermentation with a microorganism production dehydrogenase alcohol to convert said D-arabitol to D-xylulose syrup, subjecting said D-xylulose to enzymatic isomerization at a temperature of 40° to 80° C. and a pH of between 6.0 and 8.5 to provide a mixture of D-xylose and D-xylulose, containing arabitol and xylitol as impurities, subjecting said mixture to chromatographic fractionation to provide at least two fractions of which one is highly enriched in D-xylose (fraction $X_1$) and has a content of this product from 60 to 95% and of which the other is highly enriched in D-xylulose (fraction ($X_2$) and has a content of this product from 50 to 80%, the percentages being expressed by weight on dry matter, recycling the fraction $X_2$ to the isomerization step, and recovering D-xylose from the fraction $X_1$.

2. Process according to claim 1, wherein the isomerizing enzyme used is selected from the group consisting of glucose isomerase and xylose isomerase.

3. Process according to claim 2, wherein the isomerizing enzyme is a glucose isomerase.

4. Process according to claim 1, wherein the chromatographic fractionation step is carried out by resorting to cationic resins or zeolites.

5. Process according to claim , wherein the chromatographic fractionation step is carried out discontinuously or continuously (simulated moving bed), on adsorbents of the highly acid cationic resin type, preferably charged with alcaline or alcaline-earth ions, or again of the cationic zeolite type charged with $NH_4^+$, $Na^+$, $K^+$ and $Ca^{2+}$, $Ba^{2+}$ ions.

6. Process according to claim 1, wherein the parameters of the enzymatic isomerization step are selected so that the latter results in a syrup with a content of D-xylose higher than 53%.

7. Process according to claim 1, wherein the parameters of the chromatographic fractionation step are selected so that there is obtained a fraction rich in xylose having a content of this product, the percentages being expressed by weight on dry matter, from 75 to 90% and a content of D-xylulose less than 25%.

8. Process according to claim 1, wherein the parameters of the chromatographic fractionation step are selected so that there is obtained a fraction rich in xylose having a content of this product, the percentages being expressed by weight on dry matter, from 80 to 85% and a content of D-xylulose less than 15%.

9. Process according to claim 1, wherein the mother-liquors from crystallization of xylose are recycled to the chromatographic fractionation step.

10. Process according to claim 1, wherein the fraction $X_1$ is subjected directly to a hydrogenation step.

11. Process according to claim 1, wherein the osmophilic microorganism is of PICHIA genus.

* * * * *